United States Patent [19]

Miller et al.

[11] Patent Number: 5,418,138
[45] Date of Patent: May 23, 1995

[54] IMMUNOHISTOCHEMICAL STAINING METHOD AND REAGENTS THEREFOR

[75] Inventors: Phillip C. Miller; Michael J. Degroff; Michael J. Gizinski; James A. Rybski; Pamela S. Vandivort; Anthony L. Hartman, all of Tucson, Ariz.

[73] Assignee: Ventana Medical Systems, Inc., Tucson, Ariz.

[21] Appl. No.: 212,415

[22] Filed: Mar. 11, 1994

Related U.S. Application Data

[60] Division of Ser. No. 924,053, Aug. 31, 1992, Pat. No. 5,322,771, which is a continuation-in-part of Ser. No. 488,348, Mar. 2, 1990, Pat. No. 5,225,325.

[51] Int. Cl.$^6$ .......................................... G01N 33/535
[52] U.S. Cl. ...................................... 435/7.2; 435/7.9; 435/28; 435/960; 435/963
[58] Field of Search .................. 435/7.2, 7.9, 28, 960, 435/963

[56] References Cited

U.S. PATENT DOCUMENTS

| | | | |
|---|---|---|---|
| 3,050,445 | 8/1962 | Damaskus et al. | 435/188 |
| 3,607,653 | 9/1971 | Ziffer | 435/188 |
| 4,379,086 | 4/1983 | Kimura et al. | 530/390.5 |
| 4,503,143 | 3/1985 | Gerser et al. | 435/7 |
| 4,543,333 | 9/1985 | Eilersten et al. | 435/188 |
| 4,615,972 | 10/1986 | Gallacher | 435/28 |
| 4,777,020 | 10/1988 | Brigati | 422/99 |
| 4,798,706 | 1/1989 | Brigati | 422/102 |
| 4,801,431 | 1/1989 | Cuomo et al. | 422/104 |
| 4,824,784 | 4/1989 | Cantarow | 435/7 |
| 4,847,208 | 7/1989 | Bogen | 436/174 |
| 4,849,342 | 7/1989 | Ben-Michael | 435/7 |
| 4,891,314 | 1/1990 | Pauly et al. | 435/28 |
| 4,965,203 | 10/1990 | Silbering et al. | 435/188 |
| 4,971,783 | 11/1990 | Bolton et al. | 424/3 |
| 5,017,471 | 5/1991 | Fellman | 435/5 |
| 5,073,504 | 12/1991 | Bogen | 436/174 |

(List continued on next page.)

OTHER PUBLICATIONS

Brigati et al., "Immunocytochemistry is Automated: Development of A Robotic Workstation Based Upon the Capillary Action Principle," *J. Histotechnology* 11:165–183 (1988).

(List continued on next page.)

*Primary Examiner*—David Saunders
*Attorney, Agent, or Firm*—Skjerven, Morrill, MacPherson, Franklin & Friel; Laura Terlizzi

[57] ABSTRACT

The present invention provides an improved method for staining slides using immunochemical reagents. The method comprises the following steps. The assay region of a slide (the region containing the tissue section) is washed with an improved rinsing solution comprising water and a detergent. An evaporation inhibitor liquid is applied to the slide to cover the assay region. For antigens requiring unmasking, the tissue section is combined with an improved, stabilized proteolytic enzyme solution. The slide is rinsed, and the evaporation inhibitor liquid is reapplied to the slide. A primary antibody in an improved diluent containing globulins from the same species as a second antibody is combined with the tissue section for a time sufficient for substantially complete antibody binding. The slide is rinsed, and the evaporation inhibitor liquid is reapplied. A labeled second antibody in the improved diluent is combined with the tissue section for a time sufficient for substantially complete antibody binding. The slide is rinsed, and the evaporation inhibitor liquid is reapplied to the slide. Color development reagents, including a stabilized peroxidase chromophore formulation, are combined with the tissue section for a time sufficient for color development. The stabilized peroxidase chromophore formulation consists essentially of a peroxidase chromophore, at a concentration in the working range of the enzyme, an acidic buffer, a reducing agent, and a glycol. Preferred chromophores include 3,3'-diaminobenzidine and tetrahydrochloride (DAB) and 3-amino-9-ethylcarbazole (AEC). After color development, the tissue section is washed and is then ready for analysis.

10 Claims, No Drawings

U.S. PATENT DOCUMENTS

| | | | |
|---|---|---|---|
| 5,192,657 | 3/1993 | Jakway et al. | 435/4 |
| 5,206,150 | 4/1993 | Tai | 435/28 |
| 5,215,885 | 6/1993 | Marrujo et al. | 435/7.94 |

OTHER PUBLICATIONS

*Biochemica Boehringer Mannheim,* "Antibodies and Reagents for Immunochemistry," pp. 129–134 (1989).

Cosgrove et al., "Design and application of an instrument for automated immuno-staining," *ACL,* pp. 23–27 (Dec., 1989).

Espinoza et al., *Manual of Clinical Laboratory Immunology,* 4th Ed., American Society for Microbiology, Washington, D.C., pp. 277–281 (1992).

Kwapinski, *Methodology of Investigative and Clinical Immunology,* Robert E. Krieger Pub. Co., Inc. pp. 244–251 (1982).

Peters, *Methods in Immunology and Immunochemistry,* vol. V, Academic Press, New York, pp. 424–427 (1976).

Stark et al., "An automated device for immunocytochemistry," *J. Immunol. Methods.* 107:89–92 (1988).

Stross et al., "Automation of APAAP immunocytochemical technique," *J. Clin. Pathol.* 42:106–112 (1989).

Unger et al., "Automation of In situ Hybridization: Application of the Capillary Action Robotic Workstation," *J. Histotechnology* 11:253–258 (1988).

IMMUNOHISTOCHEMICAL STAINING METHOD AND REAGENTS THEREFOR

This application is a division of application Ser. No. 07/924,053, filed Aug. 31, 1992, and now U.S. Pat. No. 5,322,771, which is the national phase application of PCT/US91/01108, filed Feb. 27, 1991, which application is a continuation-in-part of application Ser. No. 07/488,348, filed Mar. 2, 1990, now U.S. Pat. No. 5,225,325, filed Jul. 6, 1993.

FIELD OF THE INVENTION

The present invention relates to an improved method for immunohistochemical staining of slides, particularly an automated method, and reagents therefor.

BACKGROUND OF THE INVENTION

Four main methods using peroxidase (HRPO) are now generally recognized for immunostaining. The methods are based on the immune reaction of an antigen to be detected in the specimen complexing with an antibody specific for the antigen. The methods differ primarily in the manner of detecting the antigen-antibody complex. The methods are the direct method, an indirect method using an enzyme-conjugated secondary antibody specific for the species of the primary or first antibody, the peroxidase-antiperoxidase (PAP) method, and an indirect biotin-avidin method using a biotin-conjugated secondary antibody and a complex of a biotin-conjugated peroxidase and either avidin or strepavidin.

All of the immunohistochemistry methods, as well as other immunochemical methods, are multi-step procedures which consist of a sequence of reagent additions, incubations, and washings. Most of these procedures require highly trained personnel and the results can vary significantly between laboratories. Automated systems have been explored to introduce cost savings, uniformity of slide preparation, and reduction of procedural human errors.

For both automated and manual methods, there are a number of critical points to be considered. Care must be exercised to avoid the loss of specimen from the slide. Thorough washing of the specimen between reagent applications is essential particularly to remove unbound antibody as residues would be amplified. Excess liquid must be removed to avoid unwanted dilution of antibodies, yet specimens must never be allowed to dry out. Enough antibody reagent must be applied to completely cover the slide area where the specimen may occur, but waste has to be kept to an absolute minimum.

In addition, many of the reagents used in immunohistochemical methods as well as immunochemical methods, such as enzyme solutions and peroxidase color development reagents, have limited stability at the working-temperature and even at room temperature. This necessitates frequent preparation of the reagents. Furthermore, nonspecific antibody binding, leading to erroneous results, remains a problem.

Methods and reagents that improve results and minimize reagent preparation would facilitate both manual and automated immunohistochemical methods. Many of the improvements could be readily applied to related immunochemical methods such as enzyme-linked immunosorbent assays (ELISA), immunofluorescence assays and in situ hybridization.

DESCRIPTION OF THE PRIOR ART

Cosgrove et al, ACL pp 23–27 (December, 1989) describe immunostaining methods, particularly peroxidase staining methods, and an automated staining apparatus. Brigati and his colleagues [Brigati et al, J. Histotechnology 11:165–183 (1988); Unger et al, J. Histotechnology. 11:253–258 (1988)] describe the Fisher automated work station (which can perform immunohistochemical staining and in situ hybridization methods) and reagents used in the automated methods. The system and reagents are further described in U.S. Pat. Nos. 4,777,020, 4,798,706 and 4,801,431. Each of those devices uses a different method to conserve expensive (antibody-containing) reagents.

Stross et al, J. Clin. Pathol. 42:106–112 (1989) describes an automated tissue staining system which processes the slides following manual application of antibody-containing reagents. Stark et al, J. Immunol. Methods. 107:89–92 (1988) describes a microprocessor-controlled automated staining system.

Each of the above-described references is incorporated herein by reference in its entirety.

SUMMARY OF THE INVENTION

The present invention provides an improved method for staining slides using immunochemical reagents. In a preferred embodiment, the method is used in an automated process. The method comprises the following steps. The assay region of a slide (the region containing the tissue section) is washed with an improved rinsing solution comprising water and a detergent. An evaporation inhibitor liquid is applied to the slide to cover the assay region. For antigens requiring unmasking, the tissue section is combined with an improved, stabilized proteolytic enzyme solution. The slide is rinsed, and the evaporation inhibitor liquid is reapplied to the slide. A primary antibody in an improved diluent containing globulins from the same species as a second antibody is combined with the tissue section for a time sufficient for substantially complete antibody binding. The slide is rinsed, and the evaporation inhibitor liquid is reapplied. A labeled second antibody in the improved diluent is combined with the tissue section for a time sufficient for substantially complete antibody binding. The slide is rinsed, and the evaporation inhibitor liquid is reapplied to the slide. Color development reagents, including, in a preferred embodiment, a stabilized diaminobenzidine (DAB) solution, are combined with the tissue section for a time sufficient for color development. Following rinsing, and, optionally, DAB color enhancement and/or counterstaining, the tissue section is ready for analysis.

Improved reagents used in the method are also described.

DETAILED DESCRIPTION OF THE INVENTION

The present invention provides improved compositions and assay method steps which are useful in immunohistochemical (IHC) staining procedures generally, and, in particular, in IHC methods in which a peroxidase labeling reagent is used. However, many of the compositions and method steps have more general applicability, as will be clear to one of ordinary skill in the art.

Four main methods are now generally used for immunostaining. The methods are based on the immune reaction of an antigen of interest in the specimen complexing with an antibody specific for the antigen. The methods differ primarily in the manner the antigen-antibody complex is detected. Each of the methods uses a labeled antibody.

Labels suitable for immunoassay techniques, including IHC techniques, are well known. Those labels include labels which can be directly observed or measured such as radiolabels which can be measured with radiation counting devices; pigments, dyes or other chromogens which can be visually observed or measured with a spectrophotometer; spin labels which can be measured with a spin label analyzer; and fluorescent moieties which can be visualized under-ultraviolet light or can be measured with standard fluorometers, for example. The label can be a luminescent substance such as a phosphor or fluorogen, a bioluminescent substance, a chemiluminescent substance or a metal containing substance.

Amplification and greater distinctions from background can be achieved by use of enzyme labels or enzyme labeling systems. The enzyme breaks down a substrate to produce a chromogen, visualizing the site of the antigen/antibody complex on the slide. The substrate is selected to yield the preferred measurable product. Chromogenic and fluorogenic enzymes are preferred. These are enzymes for which substrates yielding chromogen and fluorogens, respectively, are known.

A preferred chromogenic substrate and enzyme combination uses oxidoreductases such as horseradish peroxidase and a substrate such as diaminobenzidine (DAB) and amino-ethyl carbozole (AEC) which yields a distinguishing color (brown and red, respectively). Any other enzyme/chromogen-yielding substrate combination can be used if it provides distinguishing pigmentation.

Enzyme combinations with fluorogen substrates which can be used are described in U.S. Pat. No. 4,190,496, for example, the contents of which are hereby incorporated by reference. The preferred fluorogenic substrates and suitable enzymes corresponding thereto include horseradish peroxidase for which a suitable substrate is homovanillic acid or 4-hydroxy-3-methoxyphenylacetic acid, beta-galactosidase for which a suitable substrate is 4-methylumbelliferyl-$\beta$-D-galactoside, alkaline phosphatase for which a suitable substrate is 4-methylumbelliferyl phosphate, other umbelliferyl phosphates such as 4-carboxyumbelliferyl phosphate, and umbelliferyl phosphate 4-carboxy alkylesters, etc.

In the direct method the antibody is chemically linked to a label, preferably an enzyme such as peroxidase or a fluorophore. Upon addition of the labeled antibody reagent, the antibody binds to the antigen to form an antigen-antibody/label conjugate complex. A fluorophore can be directly visualized. When the label is an enzyme, the enzyme substrate is applied, and a colored precipitate is produced at the location of the antigen-antibody/enzyme conjugate complex.

The application of the direct method is limited since a labeled antibody specific for each antigen to be detected is required. Such reagents are not generally commercially available. However, when the reagents are available and the sensitivity is sufficient, the direct method is a preferred method of antigen detection.

The second method uses a first or primary antibody specific for the antigen of interest to form the initial antigen-antibody complex. A labeled antibody, preferably an enzyme-conjugated antibody, referred to as a second or secondary antibody, which is specific for the species of the primary antibody is then used to detect the primary antibody. When the label is an enzyme, the substrate is added to detect the complex. In this way, a variety of primary antibodies produced in the same animal species can be used with a single labeled secondary antibody for visualization. In addition, enhanced sensitivity is achieved by use of the second antibody.

The third method, referred to as the peroxidase-antiperoxidase or PAP method is widely used. The PAP method has three main reagents. In addition to primary and secondary antibodies, peroxidase is complexed with an antibody against peroxidase. The secondary or link antibody is specific for the species of both the primary and the anti-peroxidase antibody. The complex is visualized using a substrate-chromogen reaction.

In the fourth method, the indirect biotin-avidin method, the secondary antibody is conjugated to the vitamin biotin. The third reagent varies dependent on the method. In the ABC method, avidin or strepavidin is added prior to or concurrently with a biotin-conjugated peroxidase. In the LAB method, the third reagent is peroxidase-labeled avidin or strepavidin. The free sites of the avidin molecule bind to the biotin on the secondary antibody. The complex is visualized with an appropriate chromogen. The strong affinity of avidin for biotin gives this method greater sensitivity than other conjugated antibody techniques.

For clarity and not by way of limitation, the invention will be described in terms of an immunohistochemical process as exemplified by an indirect biotin-avidin peroxidase method. It will be clear to one of ordinary skill in the art that the improved steps of the method can be used in other immunohistochemical processes. In fact, many of the improved steps can be used in immunochemical processes generally. Some of the reagents and steps are applicable to any small volume assay involving critical reagent concentration ranges which is performed on a slide. Those of ordinary skill in the art will also recognize that the improved reagents can be used in any HRPO staining method. Furthermore, many of the reagents can be used in other, non-peroxidase immunohistochemical staining methods as well as in other immunochemical techniques. Each of the reagents used in the exemplary method is described below in the order in which they are used in the method.

As used herein, the term "assay region" means the area of a slide to which any assay reagent(s) or sample(s) such as antibodies or tissue sections are bound. The term "tissue section" is used to refer to tissue sections (both formalin-fixed, paraffin-embedded sections and frozen sections), smears, bone marrow aspirates, cytospins, and other sample material affixed to a slide for evaluation, particularly histologic evaluation.

REAGENTS

Improved Immunochemical Rinsing Solution

Prior art assay methods wherein either the sample or an assay reagent is affixed to a slide such as immunochemical methods (including immunoassay methods and immunohistochemical staining methods) and in situ hybridization (ISH) methods utilize salted buffers to rinse the assay region of a slide between the addition of the staining or other antibody-, enzyme- or nucleic acid-containing reagents. As used herein, the term "salt" means substances that dissociate into ions in solution and includes neutral salts such as NaCl as well as the acidic, alkaline and amphoteric salts found in buffers, particularly buffers used in biological assay procedures.

The use of a salted buffer was believed necessary to reduce nonspecific antibody binding and thereby decrease the background. The presence of salt is also necessary for the specific antigen-antibody interactions, enzyme activity and nucleic acid hybridization reactions of the reagents to occur.

For assays performed on slides, the rinse solution is not completely eliminated from the slide and remains to dilute the assay reagents. In addition, large excesses of the rinse solution must be used to ensure effective dilution to remove unbound reagents in the assay region of the slide to reduce background signal. Therefore, most methods performed on slides, including immunohistochemical methods, wash with the buffer in which the next reaction is to be performed, usually phosphate buffered saline (PBS), phosphate buffer (PB) or a similar physiologic buffer.

The use of a salted buffer as a wash has drawbacks in general and created several problems in an automated system, in particular in an automated immunohistochemical system. The production of PBS is both time consuming and costly whether used in a manual or automated method. In addition, the salts contained in PBS and other physiologic buffers are harmful to an automated staining instrument. The salts build up, making cleaning difficult.

It has now been found that a substantially salt-free aqueous solution having a detergent is an effective aqueous rinse solution for washing the assay region of a slide. Surprisingly, the use of this rinse solution actually improves the staining quality in immunohistochemical preparations. In addition, the use of the improved rinse solution eliminates the harmful effects of the salts on an instrument.

It has now been found that the salts present in the reagent solutions are sufficient for good staining and that the new rinsing solution does not interfere with the reagent interactions. In addition, the improved rinse solution is both less expensive and less time consuming to prepare. Further, the solution sheets evenly, more effectively washing the slide. This is particularly important in an automated environment where the slides may not be immersed in a bath of the rinse solution.

A rinse solution of this invention consists essentially of a salt-free aqueous solution and an amount of detergent sufficient to reduce surface tension of the aqueous solution to provide for even sheeting of the rinse solution. For most applications, the salt-free aqueous solution is water. However, when enhanced preservation of nuclear morphology is desired as in immunohistochemical applications, the salt-free aqueous solution is Tris.

The salt-free aqueous solution should be free from agents that can leave a residue on the slide. Therefore, the water can be distilled or, preferably, deionized. Although water is useful as the salt-free aqueous solution in immunohistochemical staining applications, the use of Tris solutions maintains nuclear morphology without adding salt to the rinse solution and is preferred for immunohistochemical staining. Preferably, the Tris concentration is from about 0.05 to about 0.5M, more preferably about 0.1M.

As stated previously, the detergent provides for even sheeting of the rinse solution to ensure that the entire slide area is effectively rinsed. The detergent should be compatible with immunohistochemical staining reagents and immunochemical reagents in general and can be any of the nonionic biological detergents used by biochemists for the solubilization of proteins and membrane components. Polyoxyethylenesorbitans and polyoxyethylene ethers are preferred. More preferred is polyoxyethylenesorbitan monolaurate (sold under the name Tween 20) and polyoxyethylene 23 lauryl ether (sold under the name Brij 35). Both detergents are available from a variety of sources including Sigma Chemical Co. St. Louis, Mo.

Preferably the detergent is used at a concentration of about 0.01 to about 5% (v/v), more preferably at about 0.05 to about 1% (v/v), most preferably at about 0.05 to about 0.5% (v/v). In a most preferred embodiment, the concentration is 0.05%. (As used herein, unless otherwise stated, % means weight percent which is the number of grams in 100 ml total volume.) For each of the other detergent-containing solutions discussed herein, suitable detergents and their concentration ranges do not vary from those discussed herein.

The rinse solution preferably includes preservatives such as antimycotic and antimicrobial agents in an effective concentration to inhibit growth of microorganisms in the solution. Preservatives which do not interfere with immunochemical reactions are well known. Exemplary agents are gentamycin, penicillin, streptomycin and, preferably, thimerosal. Sodium azide is known to inactivate peroxidase enzyme activity and is preferably not used with HRPO IHC staining reagents. The agents are effective at concentrations in the range of about 0.001% to 0.1% and are preferably used at about 0.01 to about 0.1%, more preferably about 0.05%. For each of the other preservative-containing solutions discussed herein, suitable preservatives and their concentration ranges do not vary from those discussed herein.

A preferred rinse solution consists of about 0.1% Tween 20 and about 0.05% thimerosal in deionized water. For immunohistochemical staining, a preferred rinse solution consists of about 0.1M Tris, pH 7.6, about 0.05% Brij 35 and about 0.05% thimerosal in deionized water.

The present rinsing solution has eliminated the harmful effects of the salts on an instrument without harming staining quality. In addition, the rinsing solution is readily prepared and uses reagents which are less expensive than prior art immunochemical wash solutions. Surprisingly, it has been found that the use of this rinsing solution actually improves the staining quality. Research also indicates that the salt present in the reagent solutions are sufficient for good staining and that the use of the present rinse solution does not interfere with the reagent interactions. In particular, the use of the rinsing solution does not increase the amount of nonspecific binding in comparison to prior art buffered rinse solutions. The rinse solution can be used to rinse the assay region of a slide in any immunochemical technique, since it does not interfere with antibody binding or enzyme activity.

Evaporation Inhibitor Liquid

In immunohistochemistry or in situ hybridization reactions, it is important to prevent evaporation of the reaction mixture on the slide during incubation periods. This is particularly important where a reaction mixture has a small volume, especially when heat is used to control or enhance the reaction kinetics. If evaporation occurs, the concentration of reagents can change and the tissue section can dry out. Either of those conditions can cause erroneous results.

Traditionally, evaporation is controlled by either placing the slide in a humidified chamber or placing a glass coverslip over the slide and sealing the sides of the coverslip. Both of those methods are time consuming and cumbersome. In addition, use of a glass coverslip presents a risk that the tissue section will be removed from the slide when the coverslip is removed.

The present method controls evaporation by covering the aqueous reaction mixture with an evaporation inhibitor liquid which is immiscible in the aqueous phase and has a density less than the aqueous phase. In this way, the evaporation inhibitor liquid covers the surface of the reaction mixture and eliminates the need for the use of a coverslip or a humidified chamber.

The evaporation inhibitor liquid is useful for assays performed on a slide where a small volume of reagents are maintained at an elevated temperature (above room temperature). The evaporation inhibitor liquid is particularly useful where the concentration of the reagents is important such as in ELISA assays, ISH and IHC applications.

The evaporation inhibitor liquid consists essentially of a liquid that has the following characteristics. The liquid does not interfere with the reactions which take place in the aqueous phase. The evaporation inhibitor liquid has a boiling point which is significantly higher than the temperature at which the reactions are run. Preferably, the evaporation inhibitor liquid has a boiling point above 100° C., more preferably above 150° C. Preferably, the evaporation inhibitor liquid has a low viscosity for ease of application.

Liquids which meet these criteria are hydrocarbons, preferably non-aromatic hydrocarbons having from 6 to 18 carbons. More preferred are oils of the medium chain alkane family such as decane to hexadecane (C10 to C16). Most preferred is pentadecane.

These oils have the following properties which are useful to prevent evaporation in IHC and ISH reactions. The oils are practically inert and immiscible in the aqueous reaction mixtures used in IHC and ISH. Thus, the oils do not interfere with the chemical reaction in the aqueous phase. The oils have densities significantly less than that of water, ranging from 0.73 to 0.77, allowing them to easily float on the aqueous phase. The oils have boiling points well above the range of temperatures needed for immunohistochemical or in situ hybridization, which boiling points range from 174° C. to 280° C. This prevents the oils from evaporating during the incubation period.

In addition to the required characteristics, all of these oils have additional properties which are desirable for use in such reactions. The oils have melting points below room temperature, making them easy to dispense. The oils also have relatively low viscosities which facilitate easy dispensing and cause the oils to float on the aqueous phase. The oils are also inexpensive and available in high purity.

The evaporation inhibitor liquid is used by dropping a sufficient amount of the liquid to cover the assay region onto the slide. Use of about 500 μl is convenient.

Using an evaporation inhibitor liquid is more efficient and convenient than prior art methods using glass coverslips or humidified chambers. The evaporation inhibitor liquid is easily floated over the aqueous phase by simply applying a few drops of the liquid to the slide.

The evaporation inhibitor liquid is also readily removed by washing the slide with a small amount of water. In addition, because of the dynamic nature of the evaporation inhibitor liquid phase, the aqueous phase reagents can be added in any sequence, as the aqueous phase sinks through the evaporation inhibitor liquid phase, ensuring that no evaporation takes place prior to addition of the coverslip or placement in the chamber as in prior art methods.

The aqueous phase can be mixed with the evaporation inhibitor liquid in place. The aqueous phase can be mixed by placing the slide on a conventional agitator. A preferred automated apparatus mixes the aqueous phase by directing air jets onto the slide. That apparatus is described in Example 3. The evaporation inhibitor liquid effectively retains the aqueous phase reagents in place on the slide during mixing.

It should be noted that for ISH reactions the DNA is typically melted at about 95° C. The evaporation inhibitor liquid is completely effective at 95° C. Humidity chambers used in prior art reactions to prevent evaporation are not effective since the vapor pressure inside the typical chamber is not high enough to prevent evaporation.

Endogenous Peroxidase-Inhibition Solution

The IHC staining method preferably includes a step where the tissue section is incubated with a solution of hydrogen peroxide ($H_2O_2$) prior to use of any of the antibody reagents to eliminate endogenous peroxidase activity. As is well known, a conventional solution of 3% $H_2O_2$ in water is effective, as is a solution of 1.0% $H_2O_2$, 0.1% azide. Preferably, the solution includes a physiologic buffer, e.g. Tris buffer, phosphate buffer (PB), citrate buffer, phosphate buffered saline (PBS). A most preferred buffer is 0.1M PBS, pH 7.3, 0.1% Tween 20.

An incubation of about 4 min. at 40° C. is usually sufficient to eliminate endogenous peroxidase activity.

Stabilized Proteolytic Enzyme

A protease solution is applied to paraffin-embedded, formalin-fixed tissue sections as a pre-treatment to immunohistochemical staining with a variety of antibodies such as most antidesmin and anti-keratin antibodies. Antibodies which require such tissue treatment for antigen recognition, referred to as antigen unmasking or unmasking, have been determined empirically and are reported in the literature. The protease solution is applied prior to antibody application and, preferably, just after peroxidase treatment.

The protease is said to rescue tissue from damage done by formalin during the fixation process. Formalin fixation results in cross-linking bonds that mask the tissue antigens, thereby preventing antibody recognition of the antigens and, thus, staining from occurring. This can result in false-negative readings which can lead to misdiagnosis of the tissue sample. The protease disrupts the formalin cross-linking, exposing the tissue antigens to the labeling reagents.

A major drawback to use of the protease is that the enzyme was stable for extended periods of time only when frozen. At room temperature, the enzyme was stable for only minutes at the working dilution. This is a significant disadvantage, especially for automated methods.

The present invention provides a diluent that acts as a stabilizer for a proteolytic enzyme. In this diluent, the enzyme is stable for extended periods of time at varying degrees of temperature. In particular, the enzyme has been shown to be stable (retaining at least 90% of the original enzyme activity) in the diluent at an effective concentration after storage for 10 weeks at 2 to 8° C. and at room temperature as described in detail in Example 4. The stabilized enzyme formulation can withstand ambient shipping/mailing and repeated freeze/thawing and has a greatly extended shelf life.

The stabilized proteolytic enzyme formulation includes an effective amount of the enzyme, preferably at the working dilution, in a buffer containing a glycol, a reducing agent, a source of calcium ions, and, optionally, a preservative. A preferred stabilized proteolytic enzyme solution of this invention comprises a physiologic buffer; from about 40 to about 60% of a glycol; an effective amount of a reducing agent; a source of calcium ions in a concentration sufficient to enhance enzyme stability; and an effective amount of the enzyme.

The buffer is a physiologic buffer at a pH of from about 7.0 to about 7.5, preferably 7.4. The buffer is not a phosphate-based buffer as the calcium precipitates in phosphate buffer at an effective concentration. The buffer can be MOPS (2-[N-morpholinopropanesulfonic acid), TES (2-(-hydroxy-1,1-[bis(hydroxymethyl)-ethyl]amino) ethanesulfonic acid, hepes (N-2-hydroxyethylpiperazine-N'-2-ethanesulfonic acid), BES (2-[bis(2-hydroxyethyl)amino]ethanesulfonic acid), barbital buffer or cacodylic acid buffer, Tris maleate or, preferably, Tris/HCl at a concentration of about 0.01 to 0.1M, preferably about 0.025M.

The reducing agent can be dithiothreitol, ascorbic acid or, preferably, sodium metabisulfite (MBS). Those agents are effective to stabilize enzymes at concentrations in the range of about 0.0005 to 0.05% (For MBS, this concentration is approximately 0.026 to 2.6 mM). A preferred reducing agent is MBS at a concentration of about 0.3 mM.

The glycol can be any glycol and is preferably polypropylene glycol, polyethylene glycol or, more preferably, propylene glycol. The glycol is present in an effective amount for stabilizing an enzyme, preferably about 40 to about 60% of the diluent by volume, more preferably at about 50% (v/v).

The diluent also includes a source of calcium ions, conveniently calcium chloride, at a concentration of from about 1 to about 10 mM, preferably about 5 mM. The calcium ion source is preferably not calcium phosphate due to the calcium insolubility problems discussed previously.

The solution optionally contains a preservative. Suitable preservatives do not differ from those discussed previously.

The enzyme is a proteolytic enzyme present in at least an effective amount but can be concentrated for later dilution. A preferred concentration range is from about 0.1 to about 10 units per ml, preferably about 0.1 to about 0.5 u/ml. Most preferred for is about 0.25 u/ml. The enzyme activity can be measured using a standard casein assay and total protein based on absorbance at 280 nm.

The enzyme can be an exopeptidase (such as carboxy- and amino-peptidase, dipeptidase) or, preferably, an endopeptidase (such as pepsin, cathepsin and papain). Preferably, the enzyme is type VIII alkaline protease, available commercially from Sigma Chemical Co. A most preferred formulation is shown below in Table 1.

TABLE 1

| Stabilized Proteolytic Enzyme Formulation |
| --- |
| 50% Propylene Glycol |
| 0.025 M Tris/HCl, pH 7.4 |
| 0.3 mM Sodium Metabisulfite |
| 5 mM Calcium Chloride |
| 0.05% Thimerosal |
| 0.025 u/ml type VIII alkaline protease |

The stabilized enzyme formulation of this invention is prepared by mixing the ingredients together. Following preparation, the formulation is preferably stored at 2°–8° C., but is stable upon storage at −20° C.

Antibody Diluent for Reduction of Background Signal

Immunohistochemical staining of tissue sections utilizing a primary (or first) antibody following by a species-specific second antibody commonly results in nonspecific antibody binding which leads to nonspecific staining of the specimen. Nonspecific staining can cause misinterpretation of a result which could ultimately lead to misdiagnosis of a patient's condition.

The majority of approaches to block trig nonspecific antibody binding rely on the use of relatively concentrated dilutions (1:5 to 1:20) of nonimmune serum together with increased protein concentrations, e.g. 2 to 5% bovine serum albumin (BSA). The nonimmune serum/BSA solution is often used as a separate reagent and is usually added prior to the primary antibody reagent. Although the method reduces nonspecific binding, it does not eliminate the problem.

It has now been found that the nonspecific binding of the primary antibody is not the major source of nonspecific binding. The primary antibody's nonspecific binding can be reduced by the addition of a protein, e.g. BSA, to the solution. However, the majority of the nonspecific binding observed in IHC is due to the second or bridging antibody nonspecifically binding to the tissue section.

The present invention solves the problem of nonspecific antibody binding by including the globulin fraction of nonimmune serum from the same species as the second antibody species in the primary and secondary antibody diluents. Use of the globulin fraction in the primary and secondary antibody diluents eliminates nonspecific binding by both the primary and the secondary antibodies.

An antibody diluent of this invention consists essentially of the globulin fraction of the species of the second antibody in a suitable buffer. When a mouse monoclonal antibody is used as the primary antibody followed by a goat anti-mouse second antibody, nonspecific binding is eliminated by incorporating a high concentration of goat globulins into the diluent for both the primary and secondary antibodies. If the second antibody is a rabbit antibody, rabbit globulins would be added to both antibody diluents.

The globulin fraction can be prepared from nonimmune serum by using saturated ammonium sulfate (SAS). Alternatively, more purified globulin fractions, such as produced by DEAE cellulose purification (similar to Cohn's fraction II) can also be used. Host preferred is Cohn's fraction II/III which can be prepared by well known methods and is commercially available from a number of sources including Sigma Chemical Co. (cat. no. G 5640).

The globulins are present in the diluent in a concentration sufficient to inhibit nonspecific antibody binding. Preferably, the concentration is from about 0.1 to about 5%, more preferably from about 0.1 to about 0.5%, most preferably about 0.3% (or 3 mg/ml).

In addition to the globulins, the diluent includes a physiologic buffer which is suitable for immunochemical procedures. Suitable buffers include the physiologic buffers discussed previously and the phosphate buffers such as phosphate buffer (PB) and phosphate buffered saline (PBS). A most preferred diluent buffer is 0.1M PBS, pH 7.3.

The buffer optionally also includes a detergent and a preservative. The detergent is in an amount sufficient to reduce surface tension of the solution, as discussed previously, to provide for even sheeting of the buffer to ensure that the entire tissue section is effectively covered by the antibody solution. In addition, including the detergent in the antibody diluent buffer maintains a constant detergent concentration throughout the procedure. Suitable detergents are those discussed previously.

The diluent buffer can also include a preservative in an effective concentration to inhibit growth of microorganisms in the solution. Suitable preservatives were and their concentrations were discussed above. Sodium azide is preferably not used.

A most preferred diluent is 0.1M PBS, pH 7.3 containing 3 mg/ml (0.3%) globulins, 0.1% Tween 20 and 0.05% thimerosal. An antibody solution of this invention includes a diluent of this invention and the primary or secondary antibody at the working dilution of the antibody. As is well known, the primary antibody is specific for the antigen of interest. The secondary antibody is specific for the primary antibody and is labeled. In a preferred embodiment, the primary antibody is a mouse monoclonal antibody and the second antibody is labeled goat anti-mouse antibody. For the indirect biotin-avidin method, the second antibody is labeled with biotin. In a preferred embodiment, the second antibody is biotinylated goat anti-mouse antibody, more preferably, the Fab'2 fraction of the antibody. When using a biotinylated second antibody, the tissue section is incubated with HRPO-labeled avidin prior to color development.

An antibody solution of this invention is used in the same manner as the if antibody were diluted in a prior art formulation. The immunochemical procedure differs in that a nonimmune serum blocking step can be eliminated, as discussed below.

The use of a high concentration of the globulin improves the reproducibility of the blocking of nonspecific binding. The lot to lot variation of nonimmune serum is eliminated by the use of the purified protein fraction for blocking. The use of globulins from the species of the second antibody provides sufficient protein in the diluent to reduce nonspecific binding of the primary antibody. The use of globulins also reduces the precipitation that occurs during storage of concentrated serum dilutions used in prior art methods to block nonspecific binding. Precipitation of the reagents imparts reproducible testing because the concentration of the components of the reagents changes during storage.

Incorporating the globulin fraction of nonimmune serum of the second antibody species into both antibody diluents reduces the need for a separate blocking reagent, eliminating a step in the staining procedure and one reagent from a staining reagent kit. This streamlines the performance of the tissue staining.

Peroxidase-Labeled Avidin Solution

In the indirect biotin-avidin staining method, the tissue section is incubated with a solution of HRPO-labeled avidin. A preferred HRPO-labeled avidin is horseradish peroxidase-labeled strepavidin which is commercially available from a number of sources including Jackson Immuno Research (West Grove, Pa.). The HRPO-labeled avidin solution can be conventional. Conventional solutions include a physiologic buffer, a protein source to inhibit nonspecific binding and, optionally, a preservative. BSA is preferably not used as the protein source due to its interaction with HRPO.

Preferably, the HRPO-labeled avidin is diluted in an antibody diluent of this invention. Bovtne or another species gamma globulin can be substituted for globulins of the second antibody species for cost savings, if desired.

Stabilized Peroxidase Chromophore Formulation

Peroxidase chromophores are electron-donating chromophores that have limited stability in aqueous solutions at low concentrations, in the range of the working dilutions of the solutions. The most commonly used peroxidase chromophores for immunohistochemical use are 3,3'-diaminobenzidine tetrahydrochloride (DAB, brown insoluble end product) and 3-amino-9-ethylcarbazole (AEC, red insoluble end product). For enzyme immunoassays, ortho-phenyldiamine hydrochloride (OPD, orange-brown soluble end product) is also commonly used. Other peroxidase chromophores include 2,2'-azino-bis (3-ethylbenzthiazoline-6-sulfonic acid) (ABTS, green soluble end product); 5-aminosalicylic acid (SAS, brown soluble end product); 4-chloro-1-naphthol (4ClN, blue insoluble end product); orthodianisidine (OD, yellow-orange soluble end product) and 3,3',5,5'-tetramethylbenzidine (TMB, pale blue soluble end product).

At present, a stabilized liquid formulation of DAB is marketed by Kirkegaard and Perry Laboratories (KPL). The formulation includes a high DAB concentration (25 mg/ml), approximately ten times the working concentration, and requires storage at 4° C. at a low pH in the presence of a glycol of unknown type. The solution is stable for about 30 days at 2°–8° C. and is ready for use following dilution to a working concentration. The KPL product is not stable at 2 mcJ/ml, the working concentration, for as little as one day at 45° C. A standard stress test requires enzyme activity in antigen-specific immunostaining following three days at 45° C.

A liquid AEC solution is also available (Sigma Chemical Company). The formulation is unknown but includes a high concentration of AEC, approximately 200 times the working concentration. The formulation is diluted and hydrogen peroxide is added to form the working solution. Once diluted with added hydrogen peroxide, the working solution is probably only stable for a few hours.

For other HPRO chromophores, the user generally prepares the chromophore solutions at the working concentration and mixes the solution with dilute hydrogen peroxide fresh the day of use. Such chromophore solutions may be stored frozen prior to addition of hydrogen peroxide. In contrast, the chromophore solution of the present invention does not include peroxide and is designed to be combined with peroxide on the slide. This prevents the acceleration of the oxidation caused by mixing peroxide with the chromophore.

The present invention provides a stabilized solution having a low concentration of liquid HRPO chromophore, in the working range of the chromophore. The general range for redox chromophores is from about 1 to 2 mg/ml (about 1 to about 10 mM). For DAB, the most preferred range is from about 4.6 to 9.2 mM. In the stabilized formulation, the chromophore remains biologically active in antigen-specific immunostaining procedures following a standard three-day, 45° C. stress test. Because the stabilized formulations of this invention contain the chromophore at a working concentration, user dilution of the reagent is not required.

In addition to the chromophore, the formulation consists essentially of an acidic buffer capable of maintaining a pH of less than 6.0; an effective amount of a reducing agent for stabilizing the chromophore; and a glycol in an amount effective to stabilize the chromophore.

The buffer is an acidic buffer that maintains the pH of the stabilized solution below pH 6.0, preferably between pH 5.0 and 5.5. The buffer preferably provides an effective pH for enzyme activity (about pH 6 to 7) when the chromophore solution is added to the enzyme-containing mixture on the slide. Suitable acidic buffers are citrate phosphate, citrate acetate, acetate, succinate, phthalate, and maleate buffer. The molarity of the buffer is adjusted to provide an appropriate buffering capacity for effective enzyme activity. Selection of an appropriate buffer for a particular chromophore is within the level of skill in the art.

More specifically, DAB's immunohistochemical pH optimum is above 6.5 but DAB is most stable around pH 5. To obtain this pH change a weak citrate-phosphate buffer which, when combined with 0.02% hydrogen peroxide in PBS at pH 7.3 and the rinse solution (at pH 7.6) remaining on the slide, the pH of the reaction mixture is greater than 7.

In contrast, AEC's enzymatic pH optimum is around 5.3. Therefore, a stronger acidic buffer (e.g., 0.1M acetate, pH 5.3) is used in the chromophore formulation. Preferably for chromophores requiring a low pH for optimal activity, the hydrogen peroxide solution is also prepared in the acidic buffer. When combined with the rinse solution remaining on the slide, an "onslide" pH of less than 6 results, providing acceptable AEC staining.

In summary, buffering capacity is selected based upon the optimal pH for the chromophore and the volume, buffering capacity and pH of the liquid remaining on the individual slides. A similar buffer selection process is performed for other peroxidase chromophores based upon unique requirements of the chromophore and the staining conditions of the slide.

A preferred buffer for use with DAB is a weak buffer, preferably citrate-phosphate buffer at a concentration of between about 5 and about 10 mM, preferably between about 7 and about 8 mM, more preferably about 7.5 mM. The buffer has an acidic pH, preferably between about 4.0 and 6.0, more preferably between about 5.0 and 5.5. Most preferred is pH 5.3 so that when the DAB formulation is mixed with $H_2O_2$ on the slide to start the color development reaction, the pH of the mixture is 6.5 or above, preferably about pH 7.0, to avoid perinuclear DAB precipitation which can lead to misinterpretation of the results.

A preferred buffer for use with AEC is relatively strong acidic buffer, preferably acetate buffer at a concentration of between about 0.5 and about 0.01M, preferably between about 0.25 and about 0.05M, more preferably about 0.1M. The buffer has an acidic pH, preferably between about 4.0 and 6.0, more preferably between about 4.5 and 5.5. Most preferred is pH 5.0.

The chromophore formulation also contains a glycol and a reducing agent at effective concentrations to stabilize small molecules such as DAB and AEC. However, those concentrations and the chromophore concentration must be balanced to avoid interfering with the enzymatic activity. In this case, polyethylene glycol (PEG) at a concentration of from about 1 to about 10%, preferably about 5% is a preferred glycol with any HRPO chromophore.

The reducing agent can be those discussed previously. The concentration varies depending on the selected HRPO chromophore and also varies from lot to lot of a given chromophore due to differences in the contaminants of each lot. For example, those agents are effective to stabilize DAB at concentrations in the range of about 0.0005 to 0.05% (approximately 0.026 to 2.6 mM) and are effective to stabilize AEC at concentrations in the range of about 0.0008 to 0.008% (approximately 40 to 400 μM). An exemplary titration procedure which can be used to determine the appropriate concentration of reducing agent for any chromophore is described in detail in the examples.

A most preferred formulation for DAB is about 5% polyethylene glycol and about 1 mM sodium metabisulfite (MBS) (approximately 0.02%). A most preferred combination for AEC is about 5% polyethylene glycol and about 200 μM MBS (approximately 0.2%).

The buffer optionally contains a preservative. Suitable preservatives do not differ from those discussed previously. The buffer optionally also includes the same biological detergent as in the antibody diluent to maintain the detergent concentration in reaction mixture at a constant level throughout the procedure. The stabilized DAB formulation is prepared by adding the glycol to the buffer solution (containing the detergent, if present). The reducing agent is added to that solution, followed by addition of DAB. For AEC, the reducing agent is added following addition of AEC to the glycol-containing buffer solution. Preparation of the stabilized HRPO chromophore solutions is described in detail in the examples. Following preparation, the chromophore formulation is stored in the dark at 2° to 8° C.

The use of a stabilized HRPO chromophore formulation of this invention does not differ from the use of prior art formulations except that hydrogen peroxide is not present in the formulation and is added directly to the slide. However, the formulation is stable at working concentration. Thus the need to prepare a new working solution each day has been eliminated.

The following table illustrates a comparison of the properties of stabilized formulations of DAB and AEC of this invention and of commercially available preparations of DAB (Kirkegaard and Perry Laboratories) and AEC (Sigma Chemical Company).

TABLE 2

| FACTOR | Chromophore Formulations | | |
| --- | --- | --- | --- |
| | KPL DAB | SIGMA AEC | STABILIZED DAB/AEC |
| Acid pH of stock | Yes | N/A[1] | Yes |

TABLE 2-continued

| FACTOR | Chromophore Formulations | | |
|---|---|---|---|
| | KPL DAB | SIGMA AEC | STABILIZED DAB/AEC |
| buffer | | | |
| Stock indicator contains glycol | N/A | N/A | Yes |
| Stock indicator contains antioxidant | N/A | N/A | Yes |
| Stock indicator requires dilution before use | Yes 1:50 | Yes 1:200 | No |
| Working solution stable during stress test | No | N/T[2] | Yes |

[1]N/A: Not available from manufacturer.
[2]N/T: Not tested.

Hydrogen Peroxide Color Development Solution

In peroxidase methods, color development starts when the chromophore solution is mixed with a hydrogen peroxide solution. The $H_2O_2$ solution can be conventional. A preferred $H_2O_2$ solution includes a physiologic buffer. Suitable physiologic buffers were as described previously. Most preferred is 0.1M PBS, pH 7.3. The solution optionally also includes a detergent and a preservative, preferably 0.1% Tween 20 and 0.05% thimerosal.

The $H_2O_2$ solution is mixed with the chromophore solution and incubated with the tissue section for about 4 to about 5 min. at about 40° C.

DAB Color-Enhancement Solution

A DAB color-enhancement solution is optionally used prior to coverslipping to render the DAB color more distinct. The DAB stain is brown. Solutions of metal ions can be used to darken (copper) or change the color of the stain to black (nickel) or blue (cobalt). Copper sulfate solution in acetate buffer is preferred.

Counterstain

A counterstain is optionally used prior to coverslipping to render the immunohistochemical stain more distinct. Counterstains differ in color from the first stain and have affinity for tissues, cells or parts of cells other than those of the first stain. Numerous counterstains are well known. A preferred counterstain is hematoxylin.

METHOD

An improved immunochemical method comprises the following steps. For clarity and not by way of limitation, the method will be described in terms of a immunohistochemical process as exemplified by an indirect biotin-avidin peroxidase method using DAB as the chromophore. It will be clear to one of ordinary skill in the art an improved step of the method can be used in other immunohistochemical processes as well as other immunochemical processes such as ELISA immunoassays.

A slide containing a tissue section is washed in a rinse solution of this invention. The slide can be washed by immersing the slide in a bath of the rinse solution, preferably by sequential immersion in three baths of the solution. Alternatively, the rinse solution can be squirted onto the slide as by using a squeeze bottle. Excess liquid is removed by allowing it to drip off of the slide or by blotting the edge of the slide on an absorbent surface.

For each of the staining reagents, the tissue section is covered with the reagent during the incubation period, as is well known. For methods wherein the slides are incubated in a vertical position in a bath of the reagent, the level of the bath is sufficient to cover the entire tissue section. For slides which are incubated horizontally, about 100 to 150 μl of the reagent is usually sufficient to cover the tissue. Using 200 μl is convenient.

Incubation times vary and depend on the temperature of the incubation. Incubation periods for substantially complete antibody binding, color development and other steps of the method are well known. Many of the steps, e.g. antigen unmasking, antibody binding, and color development, are preferably performed at elevated temperatures of at least about 35° C., preferably from about 40° to about 45° C. However, with the exception of steps dependent on enzyme activity (antigen unmasking and color development), most steps can also be performed at temperatures as low as 4° C., if the incubation period is appropriately increased. The incubation period described for each of the following steps are at a preferred incubation temperature of 40° C. unless otherwise stated.

An evaporation inhibitor liquid is applied to the slide to cover the tissue section by dropping the liquid onto the wet tissue section. A sufficient amount of the liquid is added to cover the tissue section, preferably about 500 μl.

A hydrogen peroxide solution is added to the slides to eliminate endogenous peroxidase-induced interference with staining. The $H_2O_2$ solution is added to the evaporation inhibitor liquid covering the tissue section and sinks through the evaporation inhibitor liquid to the tissue section below. The $H_2O_2$ solution is incubated for a period of time sufficient to eliminate endogenous peroxidase activity, conveniently about 4 to about 6 min.

When the antibody staining reagent is specific for an antigen that requires unmasking such as desmin or keratin, the tissue section is treated with a stabilized proteolytic enzyme solution of this invention prior to addition of the primary antibody. The stabilized proteolytic enzyme solution is added to the evaporation inhibitor liquid covering the tissue section and sinks through the evaporation inhibitor liquid to the tissue section below. Following a sufficient period of incubation for antigen unmasking, optimally about 4 to about 5 min., the slide is washed and the evaporation inhibitor liquid is reapplied.

Prior to antibody application, and preferably just after peroxide treatment, a sufficient amount of the protease solution to cover the tissue section, conveniently about 200 μl, is applied to paraffin-embedded, formalin-fixed tissue. In this diluent, the protease disrupts the formalin cross-linking without causing damage to the tissue antigens. The antigens are thus exposed to the labeling reagents, allowing for more accurate results.

The incubation period is sufficient to disrupt cross-linking but not so long that the antigens are destroyed. The period depends on the temperature, enzyme concentration, tissue thickness, tissue type and amount of time in formalin. An appropriate time can be readily determined. A 4 to 5 min. incubation at 40° C., preferably, 4 min., 30 sec. incubation at 40° C. is effective in a preferred method of this invention. Following incubation, the protease solution is washed off, and the next reagent in the staining/labeling process is applied. When these ranges are not observed, over and/or under digestion of the tissue by the protease is likely to occur, which can result in destroyed antigens/masked antigens, respectively. Following the incubation, the slide is rinsed.

Following incubation, washing and reapplication of the evaporation inhibitor liquid, the labeling reagents are added to the tissue section. First, a primary enzyme solution of this invention is added to the slide. The antibody solution is incubated for a time sufficient for substantially complete antibody binding, at least about 5 min. Following incubation, washing and reapplication of the evaporation inhibitor liquid, a biotinylated-second antibody solution of this invention is added to the slide and incubated for about 5 min. Following incubation, washing and reapplication of the evaporation inhibitor liquid, the HRPO-labeled avidin solution is incubated with the tissue section for a time sufficient for substantially complete biotin-avidin binding, about 4 to about 5 min. at about 37° to 40° C.

Following incubation, washing and reapplication of the evaporation inhibitor liquid, the color development reagents are added to the slide. The color development reagents include a stabilized DAB solution of this invention and a hydrogen peroxide solution. The reagents can be mixed and then added to the slide not longer than about 15 min. prior to use. Preferably, the DAB solution is added to the slide, followed by addition of the $H_2O_2$ solution. The solutions are mixed to start the color development reaction. The solutions can be mixed on the slide by placing the slide on an agitator. Following incubation for a time sufficient for color development, about 5 min., and washing, the immunohistochemical staining procedure is complete. A DAB color-enhancement solution, preferably copper sulfate solution, and/or a counterstain are optionally added prior to cover-slipping.

The steps for an automated method do not differ from those of a manual method. Specifically, the reagents, order of addition of the reagents and incubation time and temperature do not differ. The manner in which the reagents are applied to and incubated with the tissue section, the manner in which the tissue section is rinsed and the manner in which the excess rinse solution is removed depend on the device. A preferred automated method is described in detail in Example 2.

This invention is further illustrated by the following specific but non-limiting examples. Temperatures are given in degrees Centigrade and concentrations as weight percent unless otherwise specified. Procedures which are constructively reduced to practice are described in the present tense, and procedures which have been carried out in the laboratory are set forth in the past tense.

EXAMPLE 1

Preparation of Novel Staining Reagents

Each of the novel reagents of this invention were prepared as described below.

Rinse Solution

Add 1.0 ml of Tween 20 (Sigma P-1379) and 500 mg thimerosal to one liter of distilled water to yield 0.1% Tween 20 and 0.05% thimerosal.

Stabilized Protease Formulation

Prepare 0.5M Tris/HCl, pH 7.4, by making Solution A (0.2M Trizma Base) by adding 24.2 g of Trizma base to 1 L of distilled water and Solution B (0.2M HCl). Add 50 ml Solution A, 41.4 ml of Solution B, and 108.6 ml of distilled water to yield 0.05M Tris/HCl, pH 7.4.

For 400 ml of the stabilized protease formulation, mix the following:
- 200 ml Tris/HCl buffer, pH 7.4
- 200 ml Propylene Glycol*
- 0.02 g Sodium Metabisulfite*
- 0.294 g Calcium Chloride*
- 0.20 g Thimerosal*
- 100 u Type VIII Alkaline Protease*

*Used in form purchased from Sigma Chemical Co.

Diluent for Primary and Secondary Antibody Reagents

The diluent is prepared by preparing 0.1M phosphate buffer (PBS), pH 7.3. The following reagents are added to buffer and mixed:
- 3 mg/ml (0.3%) goat globulins (Sigma Chemical Co., cat. no. G 5640)
- 0.1% Tween 20; and
- 0.05% thimerosal.

Stabilized DAB Formulation

To prepare one liter of 7.5 mM citrate-phosphate buffer, pH 5.3 dissolve the following reagents in the following in order into 800 ml of distilled water:
1. 510.5 mg of citric acid (Sigma C-712g),
2. 1.17 gm of potassium phosphate (Sigma P-5504),
3. 1 ml of Tween 20 (Sigma P-137g),
4. 0.5 g thimerosal
5. Add distilled water to 1 L.

Next, prepare 5% polyethylene glycol (PEG) (Sigma P-5413) in the citrate-phosphate buffer by dissolving 5 g of PEG in 80 ml of buffer. Then dilute to 100 ml with additional buffer. Dissolve 95.05 mg sodium metabisulfite (MBS) (Sigma S-9000) in 5 ml of citrate-phosphate buffer containing 5% PEG (100 mM MBS) to prepare Solution A. Dilute 100 μl of Solution A in 10 ml of citrate phosphate buffer containing 5% PEG (1 mM MBS) to prepare Solution B.

Dissolve 20 mg of DAB (Sigma D-5637) into 10 ml of Solution B to yield 2 mg DAB/ml of 7.5 mM citrate-phosphate buffer, pH 5.3, containing 1.0 mM sodium metabisulfite and 5% polyethylene glycol. Following preparation, store in the dark at 2°–8° C. until use.

Stabilized AEC Formulation

To prepare one liter of 0.1M acetate buffer, pH 5.0 dissolve the following reagents in the following in order into 800 ml of distilled water:
1. 9.58 gm of sodium acetate trihydrate (Sigma S-8625),
2. 1.70 ml of glacial acetic acid (Sigma A-6283),
3. 1.7 ml of Brij-35 (Sigma 430AG-6),
4. Add distilled water to 1 L.

Next, prepare 5% polyethylene glycol (PEG) (Sigma P-5413) in the acetate buffer by dissolving 5 g of PEG in 80 ml of buffer. Then dilute to 100 ml with additional buffer. Dissolve 100 mg of AEC (Sigma A-5754) into 10 ml dimethylformamide (Baker 9221-01). Add the 10 ml of dissolved AEC to 90 ml of the acetate buffer with PEG. Allow the solution to stand for 10 minutes at room temperature. Then filter the solution through Whatman #1 filter paper to yield approximately 1 mg/ml AEC, 0.1M acetate buffer, pH 5.0, 5% polyethylene glycol to prepare AEC solution.

Dissolve 40.9 mg sodium metabisulfite (MBS) (Sigma S-9000) in 10 ml of acetate buffer containing 5% PEG (21.5 mM MBS). Titrate the MBS solution into the AEC solution until the MBS inhibits the AEC reaction approximately 0.2 absorbance units. The final MBS concentration varies from about 100 to 200 μM, depending on the purity of the lot of AEC. Following preparation, store in the dark at 2°–8° C. until use. The titration was performed as described below.

The chromophore amino-ethyl carbazole (AEC) is available as an approximately 90% pure product from SIGMA Chemical Company. The chromophore is not pure and precipitation of the chromophore occurs during the solubilization procedure described in Example 1 when the AEC (dissolved in dimethylformamide) is added to the 0.1M sodium acetate buffer. Thus, the final concentration of AEC prior to the addition of MBS is not known. Hence, the amount of MBS used must be experimentally determined by titration for each batch of liquid AEC produced.

An enzymatic reaction of the AEC is performed in the presence of various concentrations of MBS to determine the MBS concentration which inhibits the AEC reaction by approximately 0.2 absorbance units. This is usually in the range of 100 to 200 μM MBS (final concentration). The reactants are described below:

a. 483.4 μl of fresh AEC (prepared as described in Example 1, prior to addition of MBS);
b. 8.4 μl of 0.3 mg Avidin-D horseradish peroxidase/ml 0.1M sodium acetate buffer, pH 5.0 containing 5% polyethylene glycol and 0.05% Brij 35 detergent
c. 8.4 μl of 180 mM hydrogen peroxide in 0.1M sodium acetate buffer, pH 5.0 containing 5% polyethylene glycol; and
d. 5.0 μl of various concentrations of MBS in 0.1M sodium acetate buffer, pH 5.0 containing 5% polyethylene glycol and Brij 35 detergent.

The titration was performed as follows. The reaction mixture is incubated for 5 minutes at room temperature. Following incubation, 100 μl of the AEC reaction mixture is added to 900 μl of deionized water (1:10 dilution). The absorbance of the diluted AEC is scanned from 800 to 400 nm with a UV-VIS spectrophotometer. The instrument is blanked with a 1:10 dilution of 0.1M sodium acetate buffer, pH 5.0 containing 5% polyethylene glycol with deionized water.

The various absorbance curves are plotted, and the peak absorbance at 480 nm for each NBS concentration is determined. From these data, the appropriate final NBS concentration is selected and sufficient NBS from the 21.5 mN stock solution is added to the bulk AEC solution. The final AEC solution containing MBS is then assayed and compared with the AEC solution without MBS to verify that the absorbance curve for the MBS-containing solution is approximately 0.2 absorbance units lower than the curve for the unstabilized formulation. The completed reagent is stored refrigerated in the dark until used.

EXAMPLE 2

Manual, Indirect Biotin-Avidin Staining Method to Detect Desmin

A deparaffinized tissue section was washed using the rinse solution by squirting approximately 10 ml from a squeeze bottle onto the slide above the tissue section. The tissue section was then covered with an evaporation inhibitor liquid by adding 500 μl of dodecane. The washing and addition of an evaporation inhibitor liquid procedure was performed in the same manner throughout the remainder of the procedure following the end of each incubation period.

A solution of 3% $H_2O_2$ in 0.1M phosphate buffered saline (0.1M phosphate, 0.055M NaCl), pH 7.7, 0.1% Tween 20 (200 μl) was added to the slide by dropping the solution onto the evaporation inhibitor liquid. The $H_2O_2$ solution was incubated for 5 min. at 40° C.

The protease solution (200 μl) was applied to the slide and incubated for 5 min. at 40° C.

For desmin, the primary antibody solution (200 μl) was mouse monoclonal anti-desmin (clone DE-R-11; Dako, Carpenteria, Calif.) diluted 1:7 within the diluent described in Example 1. After a 5 min. incubation at 40° C., the slide was washed and the evaporation inhibitor liquid applied.

The second antibody solution (200 μl), preferably biotinylated goat anti-mouse antibody, Fab'2 fraction (Jackson Immuno Research) diluted 1:50 in the diluent, was incubated for 5 min. at 40° C. After a 5 min. incubation at 40° C., the slide was washed and the evaporation inhibitor liquid applied.

Peroxidase-labeled strepavidin (200 μl) (Jackson Immuno Research) diluted 1:100 in the antibody diluent (with bovine globulins substituted for goat globulins) prepared as described in Example 1 was added to the slide and incubated for 5 min. at 40° C. The slide was washed and the evaporation inhibitor liquid reapplied.

The stabilized DAB solution (200 μl) was added to the slide. A solution of 0.02% $H_2O_2$ in 0.1M PBS, pH 7.3, 0.1% Tween 20 was added and mixed with the DAB solution to start the reaction. The mixture was incubated at 40° C. for 5 min.

The slide was rinsed. The evaporation inhibitor liquid was applied, and then the DAB color was enhanced with copper sulfate solution (0.5% $CuSO$, in 0.1M acetate buffer, pH 5.0, 0.1% Tween 20) by incubating the solution for 5 min. at 40° C. Following the DAB enhancement, the slide was rinsed, counterstained with hematoxylin, dehydrated (using alcohol/xylene) and coverslipped.

EXAMPLE 3

Automated, Indirect Biotin-Avidin Staining Method to Detect Desmin

The procedure of Example 2 was repeated using a most preferred automated staining apparatus. The apparatus is described in detail in a commonly owned, co-pending application Ser. No. 07/488,601, filed on Mar. 2, 1990, entitled AUTOMATED BIOLOGICAL REACTION APPARATUS by Copeland et al. That application is incorporated herein by reference in its entirety.

A deparaffinized tissue section was rinsed, placed in the instrument and covered with the evaporation inhibitor liquid. The slide was removed after rinsing following DAB enhancement and the remainder of the procedure was performed manually. Each of the automated steps was performed by the instrument as described in Example 2 with the exception that the incubation period was 4 min. 20 sec.

The procedure was repeated using a 4 min. 37 sec. incubation period.

EXAMPLE 4

Automated, Indirect Biotin-Avidin Staining Method to Detect Desmin

The procedure of Example 3 was repeated with the following exceptions. The stabilized AEC solution, prepared as described in Example 1, was used in place of the stabilized DAB solution, and the buffer in the hydrogen peroxide solution was 0.1M sodium acetate. Following color development, the slide was rinsed, counterstained with hemotoxylin and coverslipped with an aqueous mounting medium.

EXAMPLE 5

Study of Enzyme Activity in Stabilized Protease Formulation

Two samples of a stabilized protease formulation of this invention was prepared as described in Example 1 with the exception that one sample of the formulation omitted the thimerosal. Each solution was divided into three aliquots and placed in vials. The vials were placed in 2°–8° C., room temperature (RT, about 23° C.), and 45° C. atmospheres immediately after the enzyme activity of each batch (initial activity at Day 0) was determined using a casein solution assay. The activity of each vial at each temperature was then periodically measured for the percentage of initial enzyme activity using the same casein assay, The assay was done in triplicate and the average value was taken, Plots were made using the value of 5.0 casein units of activity (the average initial activity) as 100%. The results are illustrated in Table 2 below. The values of the enzyme activity for the formulation without thimerosal were determined at 11 weeks and with thimerosal at 10 weeks.

TABLE 2

| | Percentage of Initial Enzyme Activity | | |
|---|---|---|---|
| | 2–8° C. | RT | 45° C. |
| without thimerosal | 100 | 100 | 25 |
| with thimerosal | 92 | 100 | 42 |

As shown in the table, the stabilized protease formulation retained greater than 90% of initial enzyme activity at 2° to 8° C. and at room temperature for at least 10 weeks.

What is claimed is:

1. A stabilized aqueous peroxidase chromophore solution consisting essentially of:
    a. a peroxidase chromophore at a concentration in the working range of the peroxidase;
    b. an acidic buffer capable of maintaining a pH of less than 6.0;
    c. a reducing agent at a concentration effective to stabilize said peroxidase chromophore; and
    d. from 1 to 10% of a glycol.

2. The stabilized aqueous peroxidase chromophore solution of claim 1 wherein said peroxidase chromophore is 3,3'-diaminobenzidine tetrahydrochloride (DAB) and said acidic buffer is a citrate-phosphate buffer at a concentration of between 5 and 10 mM.

3. The stabilized aqueous peroxidase chromophore solution of claim 1 wherein said peroxidase chromophore is 3-amino-9-ethylcarbazole (AEC) and said acidic buffer is an acetate buffer at a concentration of between 0.01 and 0.5M.

4. The stabilized aqueous peroxidase chromophore solution of claim 1 wherein said reducing agent is selected from the group consisting of dithiothreitol, ascorbic acid and sodium metabisulfite.

5. The stabilized aqueous peroxidase chromophore solution of claim 4 wherein said reducing agent is sodium metabisulfite.

6. The stabilized aqueous peroxidase chromophore solution of claim 1 wherein said glycol is polyethylene glycol.

7. The stabilized aqueous peroxidase chromophore solution of claim 1 additionally comprising a detergent in an amount sufficient to reduce surface tension to provide for even sheeting of the solution.

8. A stabilized aqueous 3,3'-diaminobenzidine tetrahydrochloride (DAB) solution comprising:
    a. 2 mg/ml DAB;
    b. from 5 to 10 mM citrate-phosphate buffer, pH 5.0 to 5.5;
    c. 0.0005 to 0.05% sodium metabisulfite;
    d. from 1 to 10% polyethylene glycol; and
    e. optionally, from 0.01 to 5% (v/v) of a nonionic detergent selected from the group consisting of a polyoxyethylenesorbitan and a polyoxyethylene ether.

9. A stabilized aqueous 3-amino-9-ethylcarbazole (AEC) solution comprising:
    a. 1 mg/ml AEC;
    b. from 0.01 and 0.5M acetate buffer, pH 4.5 to 5.5;
    c. from 0.0008 to 0.008% sodium metabisulfite;
    d. from 1 to 10% polyethylene glycol; and
    e. optionally, from 0.01 to 5% (v/v) of a nonionic detergent selected from the group consisting of a polyoxyethylenesorbitan and a polyoxyethylene ether.

10. An improved immunochemical method wherein an antibody is added to a reaction mixture, said antibody being directly or indirectly labeled using an enzyme system including a peroxidase and a peroxidase chromophore, the improvement comprising combining a stabilized aqueous peroxidase chromophore solution consisting essentially of a peroxidase chromophore at a concentration in the working range of said peroxidase chromophore; an acidic buffer capable of maintaining a pH of less than 6.0; a reducing agent at a concentration effective to stabilize said peroxidase chromophore; and a glycol at a concentration effective to stabilize said peroxidase chromophore with said peroxidase.

* * * * *